United States Patent [19]

Sinnett

[11] Patent Number: 4,784,138
[45] Date of Patent: Nov. 15, 1988

[54] METHOD FOR IMPLANTING RETINAL TACK

[75] Inventor: Kevin B. Sinnett, Mukwonago, Wis.

[73] Assignee: Trek Medical Products, Inc., Oak Creek, Wis.

[21] Appl. No.: 75,395

[22] Filed: Jul. 20, 1987

Related U.S. Application Data

[60] Division of Ser. No. 4,798, Dec. 5, 1986, Pat. No. 4,712,550, which is a continuation of Ser. No. 720,988, Apr. 8, 1985, abandoned.

[51] Int. Cl.[4] ...................... A61B 17/04; A61B 17/00
[52] U.S. Cl. ............................ 128/334 R; 128/303 R
[58] Field of Search ..................... 128/334 R, 1.4, 303

[56] References Cited

U.S. PATENT DOCUMENTS 3,656,481  4/1972  Ness ..................................... 128/1.4
3,996,935  12/1976  Banko ................................. 128/305

OTHER PUBLICATIONS

American Journal of Ophthalmology, Feb. 1983, pp. 260-261.

Primary Examiner—Richard C. Pinkham
Assistant Examiner—Gary Jackson
Attorney, Agent, or Firm—Glenn A. Bus'

[57] ABSTRACT

The retinal tack includes a generally conical, sharply pointed forward end portion for piercing through the retina, choroid, and sclera, an elongated, generally cylindrical retaining portion having a longitudinal dimension approximating the thickness of a patient's retina, choroid, and sclera and including one or more peripheral grooves for receiving sclera tissue displaced during insertion of the forward end portion, and an enlarged head having a radially extending flange portion for engaging the retina in the area of the opening formed in the retina. The tack is carried in the tip of a tubular probe selectively connected in fluid communication with sources of negative and positive pressures and the head includes a seat portion which sealingly engages a complementary seat in the probe tip when a negative pressure is applied to the probe. The probe is inserted into the vitreous cavity through an opening in the eyeball and the tack is manually pushed through the retina, choroid, and sclera in the vicinity of the retinal tack until the head engages the retina and the retina is moved against the choroid. After a small positive pressure is introduced into the probe, it is moved away from the tack and withdrawn from the vitreous cavity.

9 Claims, 1 Drawing Sheet

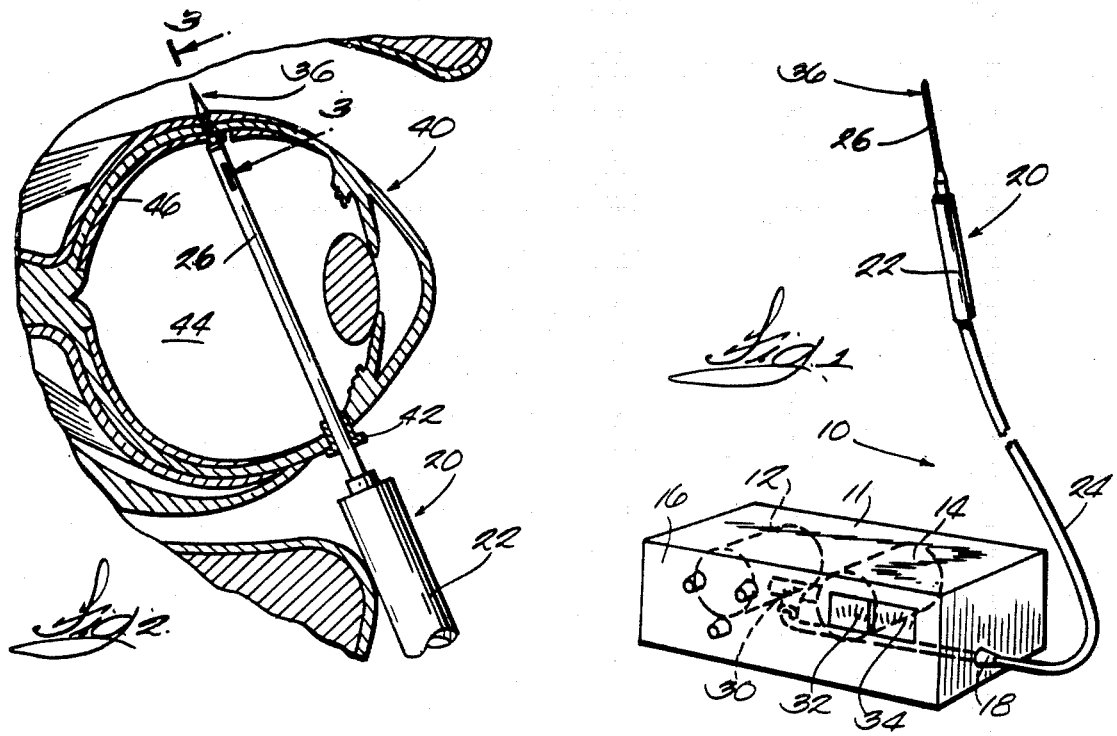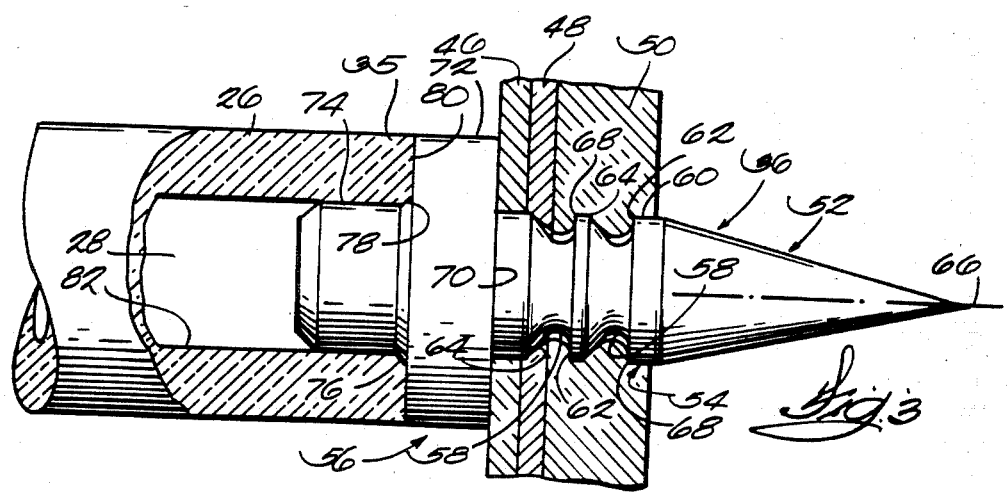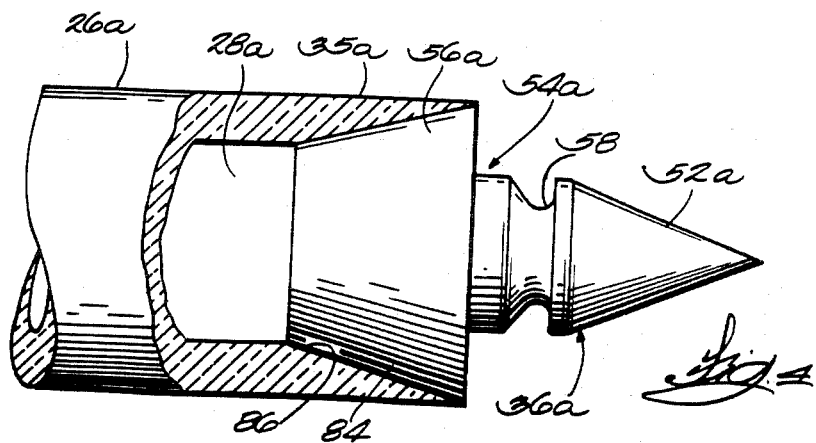

METHOD FOR IMPLANTING RETINAL TACK

This is a division of application Ser. No. 004,789 now U.S. Pat. No. 4,712,550 which was filed on Dec. 5, 1986 and is a continuation of Ser. No. 720,988 which in turn was filed on Apr. 8, 1985 and is now abandoned.

BACKGROUND OF THE INVENTION

This invention relates to ophthalmological corrective surgery and, more particularly, methods for reattaching a detached retina.

Various techniques have been proposed for reattaching a detached retina to the choroid. One approach involves injecting a silicone oil or a gas into the vitreous cavity of the eye. Some question remains with respect to the safety of intravitreous silicone oil and gas injection requires the patient to remain prone.

Another approach involves the use of one or more sutures. This approach can be hazardous and, therefore, has not been widely accepted.

A further approach involves the use of a retinal tack which is held with a mechanical device, such as intraocular forceps, and inserted through the retina into the choroid and sclera. *American Journal of Ophthalmology*, Vol 95, No. 2, p. 260 (February 1983) describes a plastic tack including a relatively short barb, a tapered section behind the barb, and a relatively long and massive head including slots to facilitate grasping by the forceps. This retinal tack has been found to have a tendency to "pop out" of the sclera within a relatively short time after surgery and, therefore, is not being widely used. Retinal tacks including several barbs have been proposed. While retention is improved somewhat, such tacks are difficult to remove in the event of a retinal tear.

SUMMARY OF THE INVENTION

An object of the invention is to provide a method for conveniently implanting a retinal tack for reattaching a detached retina to the choroid.

Other objects, aspects and advantages of the invention will become apparent to those skilled in the art upon reviewing the following detailed description, the drawing and the appended claims.

The invention provides a retinal tack including a pointed forward end portion for piercing through the retina, choroid, and sclera, an elongated retaining portion having a longitudinal dimension approximating the thickness of a patient's retina, choroid, and sclera and including one or more peripheral grooves for receiving sclera tissue displaced by the forward end portion, and an enlarged head having a radially outwardly extending flange for engaging the retina in the are a surrounding the opening formed by the forward end portion.

In one embodiment, the forward end portion is generally conical, the retaining portion has a generally cylindrical surface, each groove has radially outwardly extending forward and rear side walls, and the groove forward side wall forms a sharp corner with the outer surface with the retaining portion. The rear side wall of each groove preferably is outwardly inclined in a rearward direction to facilitate withdrawal of the tack in the event of a retinal tear or the like.

The retinal tack is releasably carried on the tip of a tubular probe selectively connected in fluid communication with sources of subatmospheric and superatmosperic pressure and the head includes a seat portion which is received by and sealingly engages a complementary seat in the probe tip.

In one embodiment, the head includes a collar extending rearwardly from the flange, a reduced stub portion which fits inside the probe tip, and a chambered portion which connects the stub portion with a collar and sealingly engages a seat in the probe tip.

The retinal tack is releasably held in the probe tip by a negative pressure in the interior passage of the probe. The probe is inserted into the vitreous cavity through an opening in the eyeball and the tack is manually inserted through the retina, choroid, and sclera in the vicinity of the retinal tear until the head engages the retina and the retina is moved against the choroid. A small positive pressure then is introduced into the interior passage of the probe to permit the probe to be moved away from the tack and withdrawn from the vitreous cavity through the eyeball opening.

BRIEF DESCRIPTION OF THE DRAWING

FIG. 1 is a perspective, partially schematic view of a system for implanting a retinal tack of the invention.

FIG. 2 is a cross-sectional view of a patient's eye with the implantation instrument probe shown in position after implantation of a retinal tack.

FIG. 3 is an enlarged sectional view taken generally along line 3—3 in FIG. 2.

FIG. 4 is an enlarged view of an alternate arrangement for the retinal tack and the implantation instrument probe.

DESCRIPTION OF THE PREFERRED EMBODIMENTS

FIG. 1 illustrates a system 10 for implanting a retinal tack of the invention. The system 10 has a conventional pump assembly 11 including a vacuum pump 12 and an air pump 14 (both illustrated schematically) driven by an electric motor (not shown) and suitably housed in a cabinet 16. The vacuum pump 12 and the air pump 14 are connected in fluid communication with an outlet fitting 18. The system 10 also has an implantation instrument 20 including a cylindrical housing 22 having an interior passage which is connected in fluid communication with the outlet fitting 18 via a flexible hose or conduit 24.

The implantation instrument 20 includes a needle-like, tubular probe 26 which resembles a needle for a hypodermic syringe and usually has an outside diameter of about 0.04 inch or less. The probe 22 has an interior passage 28 (FIG. 3) connected in fluid communication with the interior passage of the housing 22 and, thus, with the outlet fitting 18 of the pump assembly 11.

The interior passage 28 of the probe 26 is selectively connected in fluid communication with the vacuum pump 12 and the air pump 14 by an electrically-operated control valve 30 (illustrated schematically). The control valve 30 is moved between "vacuum" and "pressure" positions by operation of a suitable hand- or foot-operated switch (not shown). The outlet pressure of the vacuum pump 12 and the air pump 14 is indicated respectively by pressure gauges 32 and 34 on the front of the cabinet 18.

The vacuum pump 12 is adjusted to provide a negative or subatmospheric pressure in the order of 19 in. Hg at the tip 35 of the probe 26. The air pump 14 is adjusted to provide a small positive or superatmospheric pressure in the order of 20 mm Hg at the tip 35 of the probe 26. Referring to FIGS. 2 and 3, a retinal tack 36, including a piercing portion and a retaining portion described in more detail below, is carried by the probe tip 35 and is releasably held therein by a negative pressure in the order of 19 in Hg created in the interior passage 28 of the probe 26 by moving the control valve 28 to the "vacuum" position.

Referring to FIG. 2, a 20-gauge wound is made in the eyeball 40 at an appropriate location and a standard cannula 42 is inserted therein and sutured in place to serve as a port. While observing the interior of the eyeball through a ophthalmosope or surgical microscope, a probe having a blunt end (not shown) is introduced into the vitreous cavity 44 through the cannula 42 and manipulated to lay the detached retina 46 back into place against the choroid 48. This probe is withdrawn from the vitreous cavity and the implantation instrument probe 26 carrying a retinal tack 36, with the control valve 28 in the "vacuum" position, is introduced into the vitreous cavity 44 through the cannula 42.

The retinal tack 36 is positioned against the retina 46 at a location close to the tear and the piercing portion of the retinal tack 36 is manually pushed through the retina 46, choroid 48 and the sclera 50 until the retina 46 is moved against the choroid 48. The control valve 30 is then moved to the "pressure" position to create a positive pressure in the order of 20 mm Hg in the interior passage 28 of the probe 26. This small positive pressure assists in releasing the probe 26 from the retinal tack 36 and prevents the intraocular pressure in the vitreous cavity 44 from forcing vitreous fluids out through the probe 26. However, this pressure is low enough to prevent the retinal tack 36 from being driven further into the choroid 48 and/or the sclera 50.

Depending on the extent of the retinal tear, two or more retinal tacks 36 may be required to hold the detached retina 46 in place.

FIG. 3 illustrates a preferred embodiment of the retinal tack 36. The tack 36 includes a piercing portion 52 in the form of a sharply pointed forward end, an elongated retaining protion 54 extending rearwardly from the forward end 52 and an enlarged head 56 extending rearwardly from the retaining portion 54.

The forward end portion 52 preferably is generally concial and has a point which is as sharp as possible in order to minimize tearing of the retina 46, choroid 48 and sclera 50 during insertion therethrough.

The retaining portion 54 has a longitudinal dimension approximating the thickness of the retina 46, choroid 48 and sclera 50 and includes one or more peripherial grooves for receiving sclera tissue displaced during insertion of the forward end portion 52 therethrough. The retaining portion 54 preferably has a generally cylindrical outer surface 60. The outermost diameter of the retaining portion 54 preferably is substantially constant along the length thereof and is equal to or greater than the maximum outer diameter of the forward end portion 52.

The sclera 50 tends to conform to the exterior of the retaining portion 54 and portions of the tissue extending into the grooves 58 assist in retaining the tack 36 in place. Each groove 58 has radially extending front and rear side walls 62 and 64. To further enhance retention, the forward side wall 62 preferably extends generally perpendicularly to the longitudinal axis 66 of the tack 36 and forms a sharp corner 68 with the outer surface 60. The included angle of the corner 68 between the outer surface 60 and the forward side wall 62 preferably is about 90° or less. It has been found that rounded corners or corners of an obtuse angle generally provide poorer retention. It also has been found that providing the retaining portion 54 with a generally cylindrical outer surface provides better retention, probably because the sclera tissue applies a more uniform pressure on a larger suface area.

To facilitate removal of the tack 36 after implantation in the event of a retinal tear or the like, the rear wall 64 of each groove 58 preferably is outwardly inclined in a rearward direction.

The head 56 includes a radially outwardly extending flange 70 which engages the retina 46 in the area surrounding the opening formed by the piercing portion 52. The head 56 preferably has a circular cross section and the flange 70 preferably extends generally perpendicularly to the longitudinal axis 66 of the tack 36. The head 56 also includes an annular seat portion adapted to be received by and sealingly engage a complementary seat on the probe tip 35.

In the embodiment illustrated in FIG. 3, the head 56 has a circular collar 72 extending rearwardly from the flange 70, a reduced, generally cylindrical stub portion 74 extending rearwardly from the collar 72 and an annular, chamfered seat portion 76 connecting the stub portion 74 with the collar 72. The seat portion 76 is tapered radially inwardly in a rearward direction.

The stub portion 74 fits snugly inside the interior passage 28 of the probe 26 and the seat portion 76 sealingly engages a complementary annular seat 78 in the probe tip 35 when a negative pressure exists in the interior passage 28. Surface contact between the outer end 80 of the probe tip 35 and the collar 72 and between the wall 82 of the probe interior passage 26 and the stub portion 74 provides lateral support (i.e., resistance to torque applied on the forward end of the tack 36) against breaking the seal between the tack seat portion 76 and the probe seat 78 when the tack 36 is being implanted. Breakage of this seal could cause the tack 36 to fall away from the probe 26 and drop into the vitreous cavity 44.

The reduced diameter of the stub portion 74 facilitates grasping with a foreign body foreceps in the event the tack 36 is accidentally dropped into the vitreous cavity 44.

The outer dimension of the head 56 is 19-guage (about 0.04 inch) or less so that it can fit through a standard cannula for a 20-gauge wound. The overall length of the tack 36 will vary and depends primarily on the thickness of the retina, choroid, and sclera of a particular patient. That is, the retaining portion 54 of tacks used in adult patients is longer than that for tacks used in children. As a guide, the overall length of the tack 36 can be in the order of about 0.06 to 0.11 inch. The retaining portion 54 can have a length of about 0.01 to 0.02 and an outer dimension about 0.02 inch. The piercing section 52 can have a length of about 0.025 to 0.045 inch. The overall length of the head 56 can be about 0.02 to 0.03 inch and the length of the stub portion 74 can be about 0.015 to 0.02 inch.

FIG. 4 illustrates an alternate embodiment of the retinal tack designed for use in children and other patients having thinner retina, choroid, and sclera. In this embodiment, the length of the piercing section 52a of the retinal tack 36a is slightly less, the length of the retaining portion 54a is shorter (but still approximately the thickness of the retina, choroid, and sclera), the retaining portion 54a includes a single groove 58 and the head has a different seating arrangement.

More specifically, the entire outer surface 84 of the head 56 is tapered radially inwardly in a rearward direction and serves as a seat which sealingly engages a complementary seat 86 in the probe tip 36a when a negative pressure exists in the probe interior passage 28a. In this embodiment, lateral support for the tack 56a depends entirely on surface contact between the tapered surface 84 of the head 56a and the probe set 86. These two surfaces are configured to provide a tight taper-to-taper fit.

The angle of taper for the head surface 84 and the probe seat preferably is about 1020 to 20°. With an angle of taper greater than about 20°, application of relatively small torques on the forward end of the tack 36a will break the seal between the head surface 84 and the probe seat 86. On the other hand, with an angle of taper less than about 10°, the walls of the probe tip 36a become quite fragile and make it more difficult to pick up tacks.

It should be understood that both the head arrangements illustrated in FIGS. 3 and 4 can be used on retinal tacks having a retaining section including one or a plurality of grooves.

The retinal tack can be fabricated from various relatively hard, inert, non-blood corrosive materials suitable for use in a human body, including commercially pure titanium and plastic materials such as polyacetals and polyethylmethacrylate. At the present time, commercially pure, Grade 4 titaminum is prefered because it can be machined to provide the desired configurational features, particarly a sharp point on the piercing portion, the sharp corner between the front side walls of the grooves and the outer surface of the retaining portion and the tapered seat on the head.

From the foregoing description, one skilled in the art can easily ascertain the essential characteristics of the invention and, without departing from the spirit and scope thereof, make various changes and modifications to adapt it to various usages.

I claim:

1. A method for securing a human patient's detached retinal to the choroid including the steps of
    providing a retinal tack adapted to be inserted through the retina, choroid and sclera and having an enlarged head portion for engaging the patient's retina after insertion;
    providing a tubular probe having a tip adapted to receive and sealingly engage the head of the retinal tack and an interior passage extending to the tip;
    placing the head of the retinal tack into the tip of the probe and reducing the pressure in the interior passage of the probe to a subatmospheric level to releasably retain the tack in the probe tip;
    inserting the probe into the patient's vitreous cavity through an opening in the eyeball and pushing the retinal tack through the retina, choroid, and sclera in the vicinity of the retinal tear until the head engages the retina and the retina is moved against the choroid;
    introducing a positive pressure in the interior passage of the probe and moving the probe away from the retinal tack; and
    withdrawing the probe from the vitreous cavity through the eyeball opening.

2. A method according to claim 1 wherein
    said tack includes a pointed forward end portion for piercing through the human patient's retina, choroid and sclera, and an elongated retaining portion extending rearwardly from said forward end position and having a longitudinal dimension approximating the thickness of the patient's retina, choroid and sclera, said retaining portion including one or more circumferentially-extending grooves for receiving sclera tissue displaced by said forward end portion during insertion therethrough;
    said head extends rearwardly from said retaining portion, has a radially outwardly extending flange portion for engaging the retina in the area surrounding the opening formed by said forward end portion and a seat portion extending rearwardly from said flange; and
    said probe has a tip including a seat for sealingly engaging said seat portion on said tack head.

3. A method according to claim 2 wherein said tack has a longitudinal axis and said flange extends generally perpendicularly to said longitudinal axis.

4. A method according to claim 3 wherein
    said forward end portion is generally conical;
    said retaining portion has a generally cylindrical outer surface; and
    each of said grooves has radially outwardly extending forward and rear side walls and said forward side wall forms a sharp corner with said outer surface of said retaining portion.

5. A method according to claim 4 wherein said rear side wall of each of said grooves is outwardly inclined in a rearward direction.

6. A method according to claim 5 wherein said retaining portion includes a plurality of said grooves in longitudinally spaced relationship.

7. A method according to claim 6 wherein
    said head includes a collar extending rearwardly from said flange and a reduced stub portion extending rearwardly from said collar; and
    said tack seat portion includes a tapered portion which is tapered radially inwardly in a rearward direction and connects said stub portion with said collar.

8. A method according to claim 5 wherein said tack includes a tapered outer surface which comprises said tack seat portion.

9. A method according to claim 8 wherein the taper of said outer surface extends at an angle of about 10° to about 20° to said longitudinal axis.

* * * * *